United States Patent
Shikata

(10) Patent No.: US 8,604,671 B2
(45) Date of Patent: Dec. 10, 2013

(54) ULTRASOUND TRANSDUCER, ULTRASOUND PROBE, AND A METHOD FOR MANUFACTURING ULTRASOUND TRANSDUCERS

(75) Inventor: Hiroyuki Shikata, Nasushiobara (JP)

(73) Assignees: Kabushiki Kaisha Toshiba, Tokyo (JP); Toshiba Medical Systems Corporation, Tochigi-Ken (JP)

(*) Notice: Subject to any disclaimer, the term of this patent is extended or adjusted under 35 U.S.C. 154(b) by 125 days.

(21) Appl. No.: 13/006,008

(22) Filed: Jan. 13, 2011

(65) Prior Publication Data

US 2011/0181149 A1 Jul. 28, 2011

(30) Foreign Application Priority Data

Jan. 28, 2010 (JP) .................................. 2010-16114

(51) Int. Cl.
    *H01L 41/08* (2006.01)

(52) U.S. Cl.
    USPC .......................................... 310/334; 310/337

(58) Field of Classification Search
    USPC .......... 310/334, 365, 337, 335, 327; 600/437, 600/439, 459
    IPC ....................................................... H01I 41/08
    See application file for complete search history.

(56) References Cited

U.S. PATENT DOCUMENTS

| 5,435,313 A | 7/1995 | Noda et al. |
|---|---|---|
| 7,745,977 B2 | 6/2010 | Aoki et al. |
| 2003/0102777 A1* | 6/2003 | Kuniyasu et al. ............. 310/334 |
| 2007/0189761 A1 | 8/2007 | Sudol |
| 2007/0276238 A1 | 11/2007 | Sudol |
| 2008/0315331 A1* | 12/2008 | Wodnicki et al. ............. 257/414 |

FOREIGN PATENT DOCUMENTS

| CN | 1890031 A | 1/2007 |
|---|---|---|
| JP | 61-118099 A | 6/1986 |
| JP | 3-254739 A | 11/1991 |
| JP | 5-103397 A | 4/1993 |
| JP | 2002-027593 A | 1/2002 |
| JP | 2004-120320 A | 4/2004 |
| JP | 2005-342337 A | 12/2005 |
| JP | 2007-513563 A | 5/2007 |
| JP | 2007-515268 A | 6/2007 |
| JP | 2008-509774 A | 4/2008 |
| JP | 2008-509775 A | 4/2008 |
| JP | 2009-044718 A | 2/2009 |
| KR | 10-2007-0066883 A | 6/2007 |

OTHER PUBLICATIONS

KR Office Action dated Jun. 14, 2012 for corresponding KR Application No. 10-2011-0003503.
Chinese Office Action with English Summary for Chinese Patent Application No. 201110036947.4 mailed on Feb. 21, 2013.
Japanese Office Action with English Translation for Japanese Patent Application No. 2010-016114 mailed on Oct. 1, 2013.

* cited by examiner

*Primary Examiner* — Thomas Dougherty
*Assistant Examiner* — Karen B Addison
(74) *Attorney, Agent, or Firm* — Yoshida & Associates, LLC

(57) ABSTRACT

In the ultrasound transducer of the present embodiment, front surface electrodes and rear surface electrodes are provided for a plurality of ultrasound vibrators. A circuit board is disposed on the rear surface side of the ultrasound vibrators, and connected to the rear surface electrodes. An electronic circuit is connected to the surface opposite to that of the rear surface electrodes side on the circuit board, and has signal paths to each ultrasound vibrator through the circuit board. A backing material is disposed on the rear surface side of the ultrasound vibrators, and is provided so as to sandwich between it and the ultrasound vibrators the circuit board and the electronic circuit.

10 Claims, 11 Drawing Sheets

Related Art

Related Art

Related Art

Related Art

Related Art

Related Art

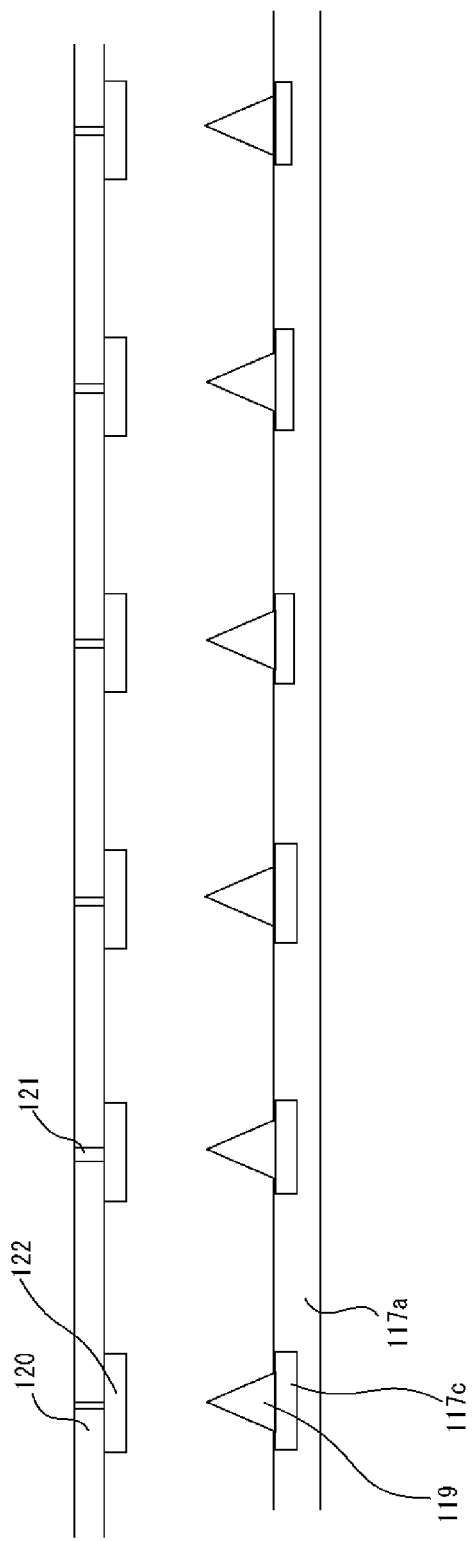

ULTRASOUND TRANSDUCER, ULTRASOUND PROBE, AND A METHOD FOR MANUFACTURING ULTRASOUND TRANSDUCERS

CROSS-REFERENCE TO RELATED APPLICATION(S)

This application is based upon and claims the benefit of priority from Japanese Patent Application No. 2010-16114 filed Jan. 28, 2010; the entire contents of which are incorporated herein by reference.

FIELD

The present embodiment relates to the technology in an ultrasound probe, an ultrasound transducer and a method for manufacturing ultrasound transducers.

BACKGROUND

An ultrasound imaging apparatus, in order to obtain, by means of an ultrasound probe, information on a body part for which a subject requires a diagnosis, transmits ultrasound to this body part.

Additionally, through the ultrasound probe, reflected waves are received from tissue boundaries within the subject, which have different acoustic characteristic impedance values. In this way, the ultrasound imaging apparatus scans ultrasound by means of the ultrasound probe, obtains information on tissues within the subject's body, and converts it into images. Diagnosticians, etc., are able to use these images to perform diagnoses. The ultrasound probe has an ultrasound transducer for the purpose of sending ultrasound waves to the subject, etc., and receiving reflected waves.

In recent years, there have been ultrasound probes that use a rotating or oscillating 1D array ultrasound transducer in the ultrasound probe. Moreover, there have been ultrasound probes based on an electronic scanning method, using a 2D array ultrasound transducer in which ultrasound vibrators (piezoelectric transducers) are disposed in the form of a matrix. Using these ultrasound probes, the study of systems for three-dimensionally acquiring ultrasound images and for displaying them has been progressing. Ultrasound images in 3D are useful in the diagnosis of body parts that are easily overlooked with 2D images. Moreover, with 3D images, it is possible to obtain tomographic images that are suitable for diagnosis or measurement, and an improvement in diagnostic accuracy can be expected.

One example of such an ultrasound probe is one in which an electronic circuit that sends and receives electric signals is embedded within the interior of its handle. The electronic circuit disposed within this ultrasound probe is connected to each of the ultrasound vibrators in the ultrasound transducer. This electronic circuit, based on control signals from the ultrasound imaging apparatus main unit, generates transmission pulses and transmits them to each ultrasound vibrator.

Moreover, this electronic circuit provides batch processing, etc., for electric signals that have been converted by the ultrasound transducer. The electronic circuit transmits the signals that have undergone batch processing to the ultrasound imaging apparatus main unit. In another example of an ultrasound probe, through a switch configured to allow modification of the connection pattern, it is also possible to have a shared connection to a plurality of ultrasound vibrators, as a group. With this configuration, the plurality of ultrasound vibrators is connected as a batch to the transmitting/receiving circuit of the ultrasound imaging apparatus main unit.

One example of the abovementioned conventional ultrasound probe and ultrasound transducer is now explained, using FIG. 1 to FIG. 6. FIG. 1 to FIG. 6 are overview diagrams showing the conventional ultrasound transducer, electronic circuit and the wiring board connecting them, which are provided in an ultrasound probe.

In the ultrasound transducer 300, as shown in FIG. 1, ultrasound vibrators 314 are disposed in a 2D pattern. Moreover, a first acoustic matching layer 310 is disposed adjacently, corresponding to each of the ultrasound vibrators 314. In addition, a second acoustic matching layer 311 is disposed on the surface on the opposite side to the side of the ultrasound vibrators 314 of the first acoustic matching layer 310. In other words, in the ultrasound transducer 300, as shown in FIG. 1, the ultrasound vibrators 314, the first acoustic matching layer 310 and the second acoustic matching layer 311, in that order, are disposed such that they are layered. Moreover, as shown in FIG. 1, for the ultrasound vibrators 314 disposed in a 2D array, on the surfaces on the opposite side to the opposite side to the side of the first acoustic matching layer 310 (hereinafter, "rear surface"), a sound absorbent backing material 318 is provided to the plurality of ultrasound vibrators 314 as a whole.

In this way, in the ultrasound transducer 300, the backing material 318, the ultrasound vibrators 314, the first acoustic matching layer 310 and the second acoustic matching layer 311 are layered in that order, and ultrasound is irradiated in the direction of this layering.

In the ultrasound transducer 300, as shown in FIG. 1, a ground electrode 312 is formed on the surface of the boundary between the ultrasound vibrator 314 and the first acoustic matching layer 310. This boundary surface is hereinafter referred to as the "front surface".

Moreover, a signal electrode 316 is provided on the surface of the boundary between the ultrasound vibrator 314 and the backing material 318. This boundary surface is hereinafter referred to as the "rear surface". By making the ground electrode 312 and the signal electrode 316 hetero-polar electrodes, one ultrasound vibrator 314 is sandwiched by electrodes with different polarities, and by electric signals from the electronic circuit, it becomes possible to drive this ultrasonic vibrator 314.

In such a conventional ultrasound transducer 300, as shown in FIG. 2, the ground electrode 312 and the transmitting/receiving circuit are connected via a wiring pattern (not shown in the diagrams) formed on a Flexible Printed Circuit (FPC) 322. Specifically, the first acoustic matching layer 310, which is adjacent to ground electrode 312 of the ultrasound vibrator 314, and the second acoustic matching layer 311 have conductivity. The ground electrode 312 and the wiring pattern of the flexible printed circuit 322 are connected through these, and these wiring patterns are connected in a shared manner, and guided to an electronic circuit.

Meanwhile, in the ultrasound transducer 300, the signal electrode 316 and the transmitting/receiving circuit are, as shown in FIG. 3, connected via the wiring pattern 321 formed on the flexible printed circuit 320. However, with an ultrasound transducer that has a 2D array, the ultrasound vibrators are disposed in a 2D array, so compared with an ultrasound transducer that has a 1D array, the number of ultrasound vibrators increases (for example, by 10 times to 100 times). As a result of this, the number of wiring patterns greatly increases as well.

For example, in the ultrasound transducer 300, as shown in FIG. 3, in order to connect each of the signal electrodes 316 of the ultrasound vibrators 314 with a wiring pattern 321, a connection pad 321a is formed on the flexible printed circuit 320. Hence, on the connection surface with each ultrasound vibrator 314 on the flexible printed circuit 320, for only the number of multiple ultrasound vibrators 314 disposed in a 2D array, connection pads 321a are formed.

However, between the multiple connection pads 321a, additionally, for only the number of ultrasound vibrators 314, wiring patterns 321 must be formed (refer to FIG. 3). With such a configuration, the pitch of the wiring patterns 321 and connection pads 321a is extremely dense, and is extremely difficult to implement.

With the conventional ultrasound transducer 300 shown in FIG. 1 to FIG. 3, the flexible printed circuit 320 is disposed between the backing material 318 and the ultrasound vibrators 314, and a configuration is implemented that makes a connection, by means of the wiring patterns 321, to the transmitting/receiving circuit of the subsequent stage. For this purpose, the entire 2D array of ultrasound vibrators 314 is divided into a plurality of modules, and a flexible printed circuit 320 is provided for each module.

Specifically, as shown in FIG. 4, a plurality of ultrasound vibrators 314 is gathered as one module, in units of a prescribed number, and those modules are disposed in a 2D array, forming the ultrasound transducer 300. By assigning a flexible printed circuit 320 to each module formed from such a group of ultrasound vibrators 314, the number of wiring patterns 321 assigned to each module is reduced.

In this way, it becomes possible to connect the transmitting/receiving circuits 332 and 334 on the relay boards 330 that are disposed corresponding to each module, and the signal electrodes 316.

In this ultrasound transducer 300, as shown in FIG. 4, flexible printed circuits 320 and 322 are interleaved between the modules. For example, between the modules of the ultrasound vibrators 314 shown in FIG. 4, a total of four flexible printed circuits 320 and 322 are provided. Hence, compared to the pitch L1 (FIG. 4) of the ultrasound vibrators 314 within the modules, the pitch L2 of the ultrasound vibrators 314 that are between the adjacent modules becomes longer.

Specifically, the space between the vibrators disposed on the edge of a certain module and the vibrators disposed on the edge of a different, adjacent module will be larger to the extent that the flexible printed circuits 320 and 322 are interleaved between the modules.

However, when the pitch between ultrasound vibrators 314 is large, as in this case, the effect of artifacts due to side lobes increases, and there is a concern that problems will arise with respect to the reliability of the ultrasound images. Additionally, when a plurality of flexible printed circuits 320 and 322 are interleaved between the ultrasound vibrators 314, there is a concern that the precision of the mutual placement of modules will worsen. As a result, there may be a negative effect on the pulse delay control, and the precision of convergence and deflection of the ultrasound beam. Moreover, in the processes for manufacturing the ultrasound transducer, the processes for forming the ultrasound vibrator module will increase, so along with the fact that the manufacturing processes will become more complicated, the cost will increase. Moreover, as a result of the increase in the number of flexible printed circuits 320 and 322, there is a concern that the ultrasound probe may become large in size.

As shown in FIG. 1 to FIG. 3 and in FIG. 4, for this ultrasound transducer 300, an ultrasound transducer that is configured so that electrode leads are embedded in the backing material, and in the backing material, the electrode leads are exposed to the surface on the opposite side to the side in the direction of ultrasound irradiation has been proposed.

Regarding such an ultrasound transducer, the configuration of the connections between the electrodes of the ultrasound vibrators and the ultrasound imaging apparatus will now be explained, referring to FIG. 5. FIG. 5 is an overview cross-section diagram showing the configuration of a conventional ultrasound transducer.

With the ultrasound transducer 300 shown in FIG. 5, the needle-shaped electrode leads 325 that are connected to the signal electrodes 316 of the ultrasound vibrators 314 are embedded into the backing material 318. The electrode leads 325 are passed through the inside of the backing material 318 from the boundary surface with the ultrasound vibrators 314 in the backing material 318, and are exposed from the edge surface of the opposite side. Moreover, in this configuration, the electronic circuits 336 are disposed so as to be adjacent to this edge surface of the backing material 318. In addition, the electronic circuits 336 and the tips of the electrode leads 325 that are exposed to the edge surface of the backing material 318 are conductively bonded, and by connecting the electronic circuits 336 with the electrode leads 325, it becomes possible to give conductivity between the signal electrode 316 and the electronic circuits 336.

In the ultrasound transducer 300 shown in FIG. 5, after the signals from the multiple ultrasound vibrators disposed in a 2D array are batch processed by the electronic circuits 336, they are transmitted to the ultrasound imaging apparatus main unit. Hence, with the ultrasound transducer FIG. 5, modules of the ultrasound vibrators 314 are not formed as with the ultrasound transducer in FIG. 4, and it is possible to prevent a situation in which the pitch of the wiring patterns formed on the flexible printed circuits 320 are extremely dense.

However, in the ultrasound transducer 300 shown in FIG. 5, by embedding the electrode leads 325 in the backing material 318, the following problems may arise. Specifically, the backing material 318 is provided for the purpose of acoustic damping of the ultrasound vibrators 314, but embedding electrode leads 325 so as not to cause any effect on the original acoustic characteristics of the backing material 318 is difficult. Moreover, even if this task can be appropriately implemented, the manufacturing processes will be complicated.

Furthermore, there is a need to avoid cross talk between the electrode leads 325. However, the electrode leads 325 are formed at a spacing that is almost the same as that of the array pitch of the ultrasound vibrators 314, so it is difficult to secure spacing between the electrode leads 325 for the purpose of avoiding cross talk.

Additionally, the backing material 318 is configured so as to have a certain length for the purpose of acoustic damping of the ultrasound vibrators 314, but if the length of the electrode leads 325 embedded in the backing material 318 is long, then there is a concern that cross talk may more easily arise. Moreover, the process for processing so as to expose both ends of the electrode lead 325 from each edge surface of the backing material 318 is extremely complicated.

Other than the abovementioned ultrasound transducers shown in FIG. 2, FIG. 4 and FIG. 5, conventionally, ultrasound transducers configured so that the electronic circuits 327 are disposed so as to directly connect with the rear surface of the ultrasound vibrators 314 have been proposed (for example, refer to FIG. 6). As shown in FIG. 6, in this ultrasound transducer 300, the electronic circuits 327 are disposed so as to be adjacent to the rear surface of the signal electrode 316 of the ultrasound vibrators 314. Additionally, the flexible printed circuit 320 is disposed between the electronic circuit 327 and the backing material 318. With this electronic transducer 300, the signal electrode 316 of each ultrasound vibrator 314 is connected to the electronic circuit 327. Hence, the electronic circuit 327 performs processing by batching together many signals. The processed signals are transferred via the flexible printed circuit 320 that is further disposed on the rear surface of the electronic circuit 327. Hence, as shown in FIG. 6, with the ultrasound transducer 300, there is no need to embed the electrode leads in the backing material 318, and immediately beneath the ultrasound vibrators 314, processing is performed to reduce the number of signal paths, so the difficulties associated with circuits with respect to electric signal transmission are eliminated.

The electronic circuit 327 of a conventional ultrasound transducer 300 as shown in FIG. 6 receives signal input from the signal electrode 316 that is connected to the front surface, and outputs signals to the wiring pattern of the flexible printed circuit 320 that is connected to the rear surface. For this purpose, in electronic circuit 327, electrodes become necessary in the front surface and the rear surface. Regarding the ultrasound transducer 300, as a semiconductor process for the purpose of implementing such an electronic circuit 327, there are, for example, TSV (Through Silicon Via) electrodes.

In the ultrasound transducer 300, as shown in FIG. 6, the electronic circuit 327 is disposed between the ultrasound vibrator 314 and the backing material 318. The electronic circuit 327 is configured using a semiconductor material (silicon, etc.). There is a concern that, from the standpoint of acoustic characteristics such as the acoustic characteristic impedance, etc., this semiconductor material may not be compatible with the ultrasound vibrators 314 or the backing material 318, etc. For example, the acoustic characteristic impedance Z of silicon is on the order of 19.5 MRayl. In contrast with this, the acoustic characteristic impedance of ultrasound vibrators 314 made from general PZT-type piezoelectric materials is on the order of 35 MRayl, and there is a large gap between that and silicon. In such cases, the reflectivity at the boundary surface is high, and negative effects from reflected waves may arise. As a result, there is a concern that this may prove disadvantageous for sending and receiving ultrasound with the ultrasound transducer.

Hence, in the ultrasound transducer 300, as shown in FIG. 6, it is necessary, by shortening as much as possible the length in the direction from the front surface of the electronic circuit 327 to its rear surface, and specifically, by minimizing the thickness of the electronic circuit 327 as much as possible, to reduce as much as possible the effects on the acoustic characteristics of the electronic circuit 327 on the sending and receiving of ultrasound, and to avoid a situation that proves disadvantageous for ultrasound imaging.

However, along with reducing the acoustic effects from the electronic circuit 327, the implementation of TSV electrodes connecting the signal electrode 316 with the wiring patterns of the flexible printed circuit 320 is difficult owing to thickness of the electronic circuit 320. Specifically, when the electronic circuit 327 is formed with a thin profile, thus reducing the acoustic effects, it becomes difficult to utilize TSV electrodes, and it is difficult to obtain a connection at both ends of the electronic circuit 327. Conversely, when it is assumed that TSV electrodes will be used in the electronic circuit 327, the thickness of the electronic circuit 327 is increased and there is a concern that due to the acoustic effects, this will prove disadvantageous in the sending and receiving of ultrasound.

BRIEF DESCRIPTION OF THE DRAWINGS

FIG. 10A is an overview cross-section diagram showing, in an ultrasound transducer according to an embodiment, a state in which, in the process of manufacturing an ultrasound transducer, connection pads of a flexible printed circuit and terminal electrodes of electronic circuits are aligned.

DETAILED DESCRIPTION

This embodiment aims to provide an ultrasound transducer that is capable of certainly performing the sending and receiving of ultrasound.

The ultrasound transducer of this embodiment comprises a plurality of ultrasound vibrators, a circuit board, an electronic circuit and backing material. Front surface electrodes and rear surface electrodes are provided to the plurality of ultrasound vibrators. The plurality of ultrasound vibrators has piezoelectric characteristics. The circuit board is disposed on the rear surface side of the ultrasound vibrators and is connected directly or indirectly to the rear surface electrodes. The electronic circuit is connected to the opposite surface to that of the rear surface electrodes side on the circuit board. On the electronic circuit are provided signal paths to each of the ultrasound vibrators, through the circuit board. The backing material is disposed on the rear surface side of the ultrasound vibrators, and is provided so as to sandwich between it and the ultrasound vibrators the circuit board and the electronic circuit.

Below, the ultrasound transducer and ultrasound probe of the embodiment are explained referring to FIGS. 7 to 10B.

Figure 1:
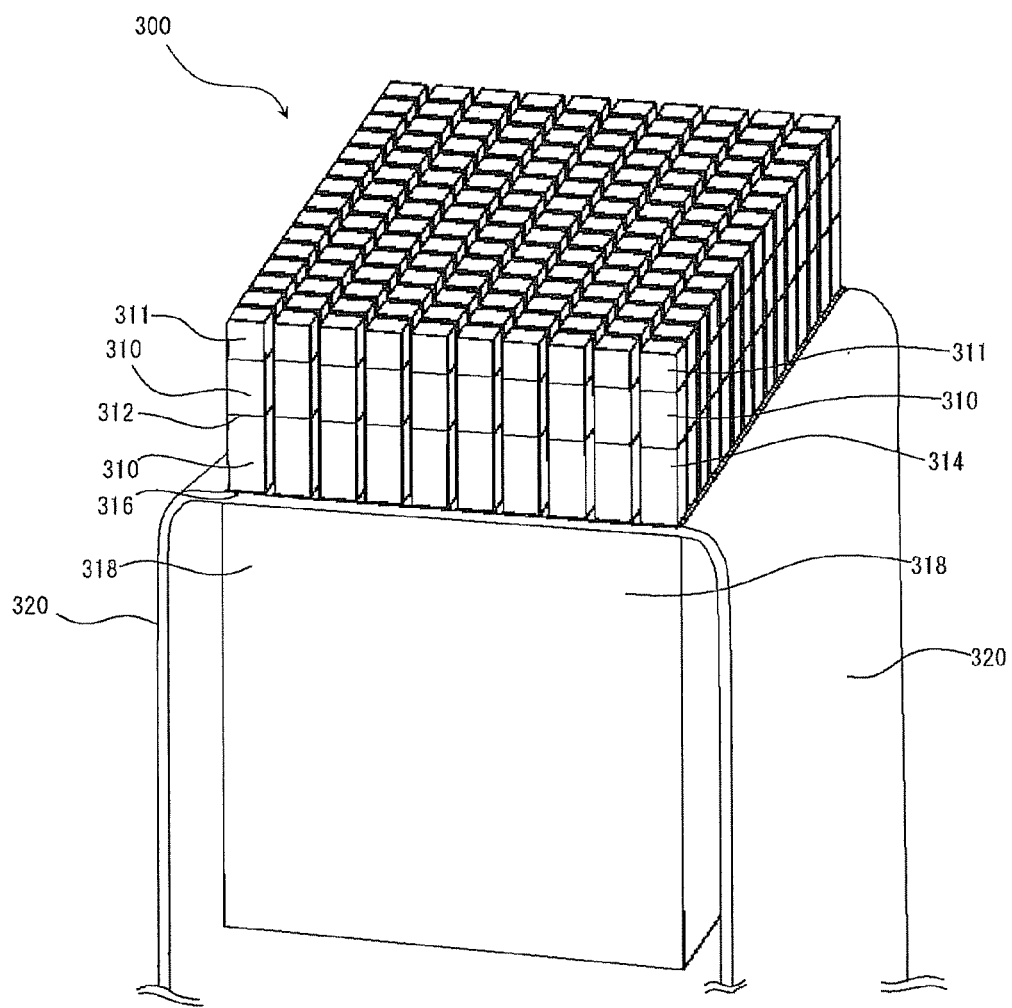
FIG. 1 is an overview perspective diagram showing a conventional ultrasound transducer which is provided in an ultrasound probe, and a wiring board connecting the ultrasound transducer and an electronic circuit.
Figure 2:
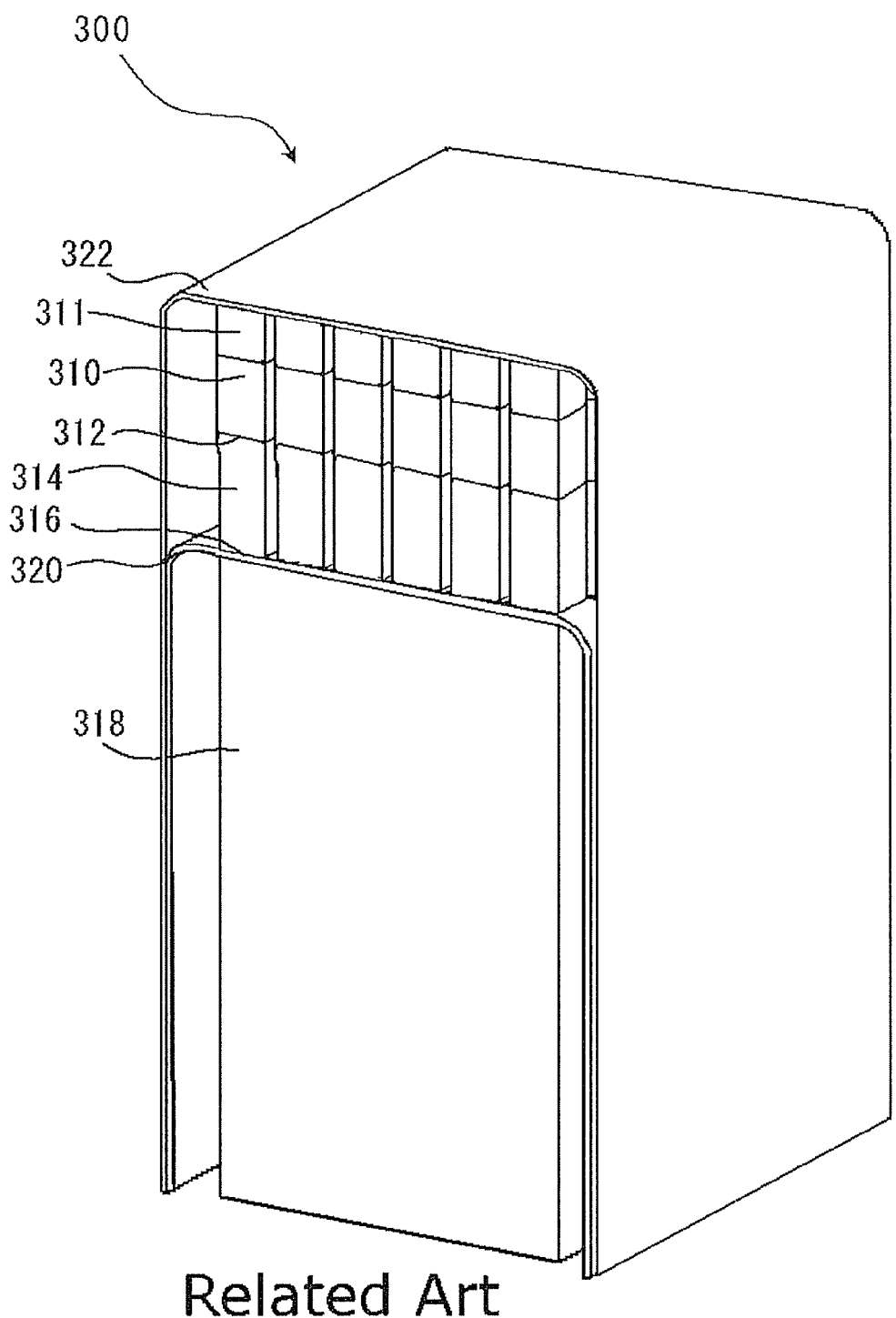
FIG. 2 is an overview perspective diagram showing a conventional ultrasound transducer which is provided in an ultrasound probe, and a wiring board connecting the ultrasound transducer and an electronic circuit.
Figure 3:
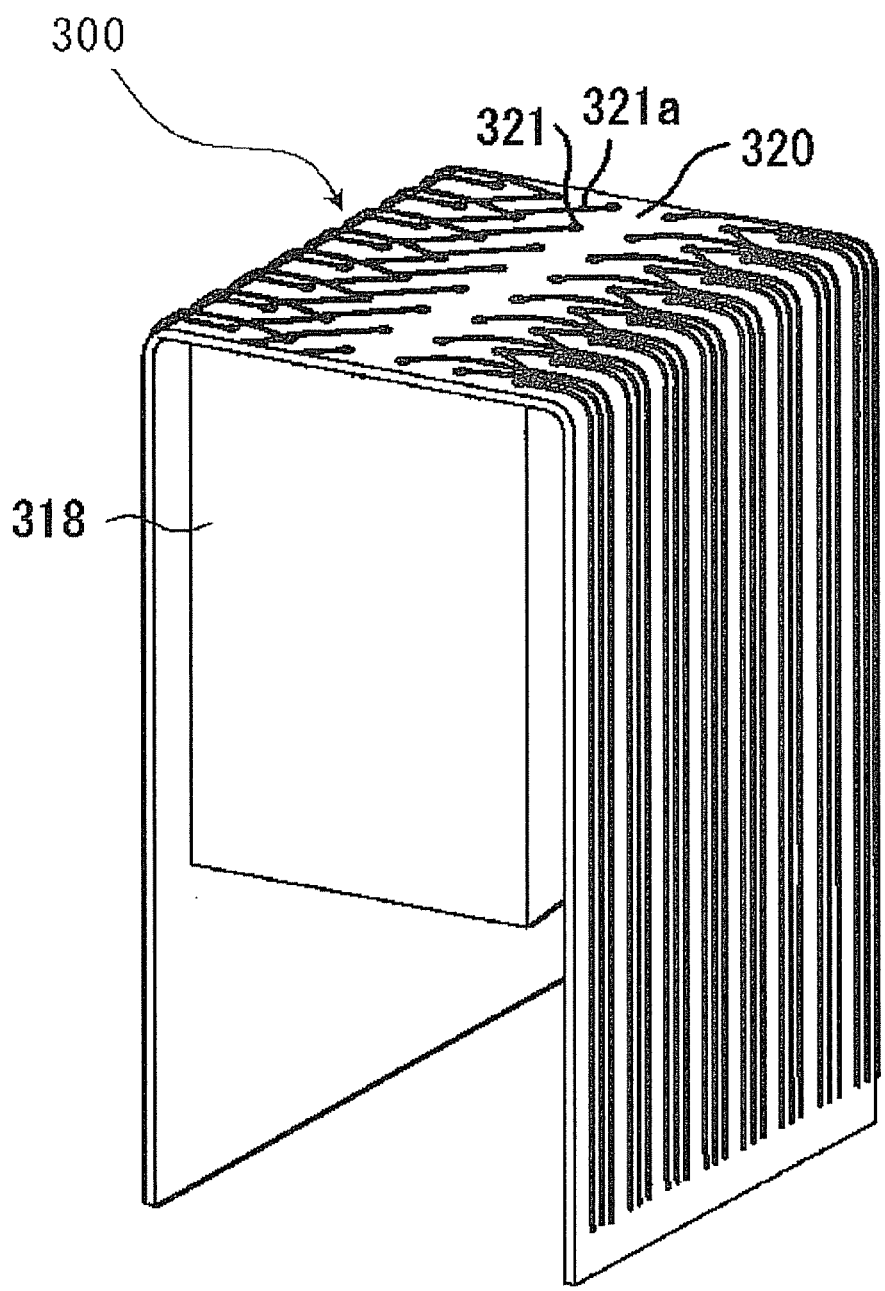
FIG. 3 is an overview perspective diagram showing a backing material of a conventional ultrasound transducer which is provided in an ultrasound probe, a wiring board and a wiring pattern.
Figure 4:
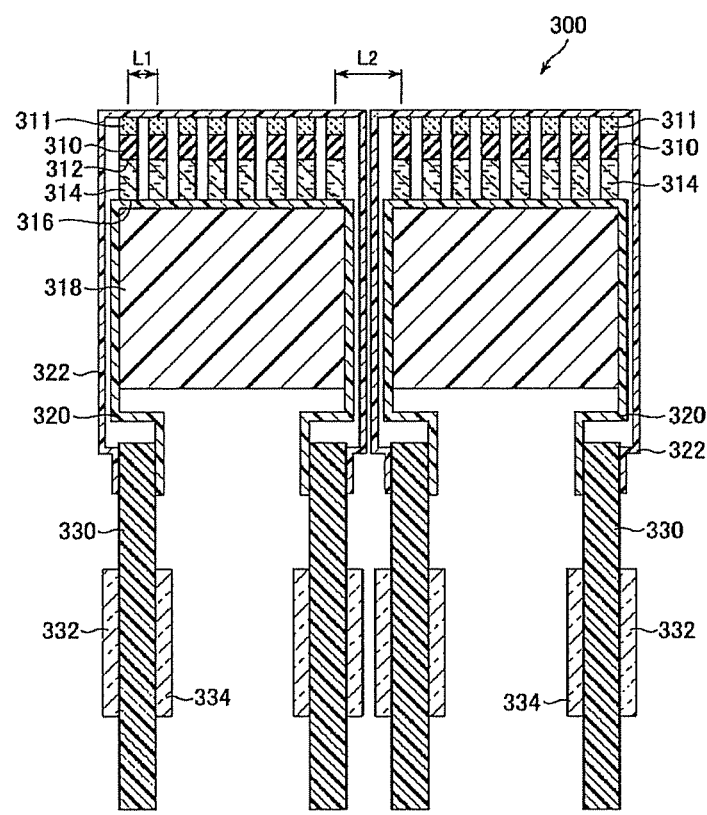
FIG. 4 is an overview cross-section diagram showing a conventional ultrasound transducer which is provided in an ultrasound probe, an electronic circuit and a wiring board connecting them.
Figure 5:
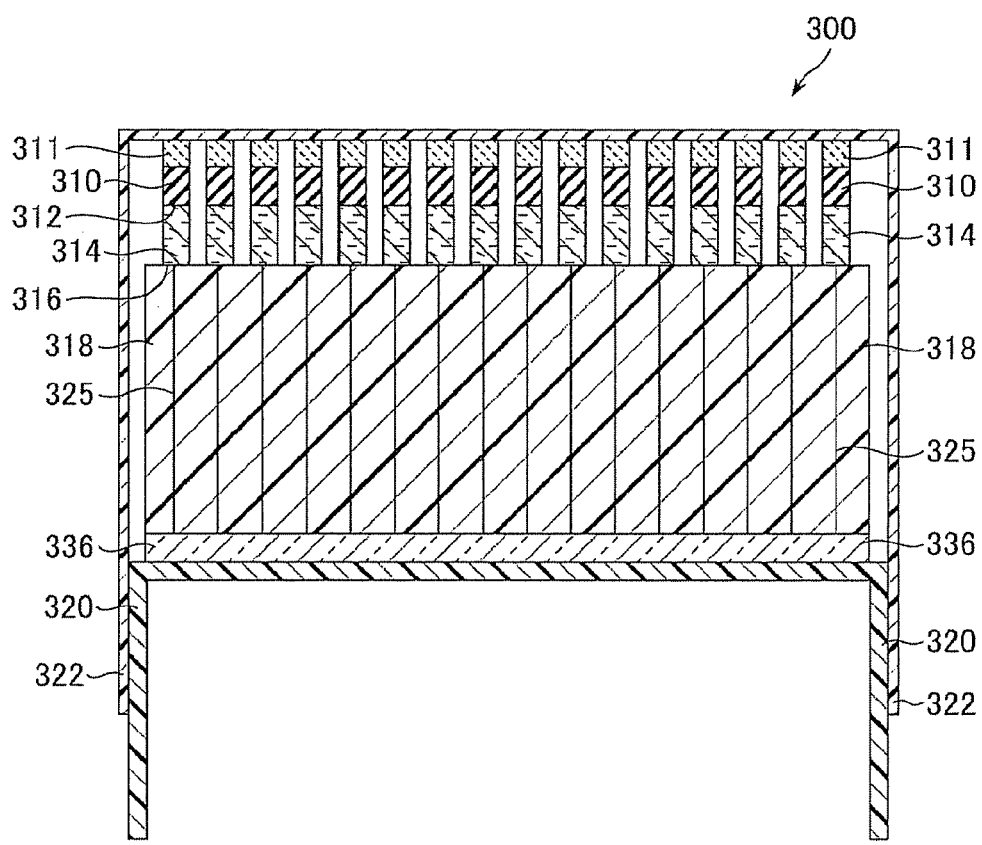
FIG. 5 is an overview cross-section diagram showing a conventional ultrasound transducer which is provided in an ultrasound probe, an electronic circuit and a wiring pattern connecting them on a wiring board.
Figure 6:
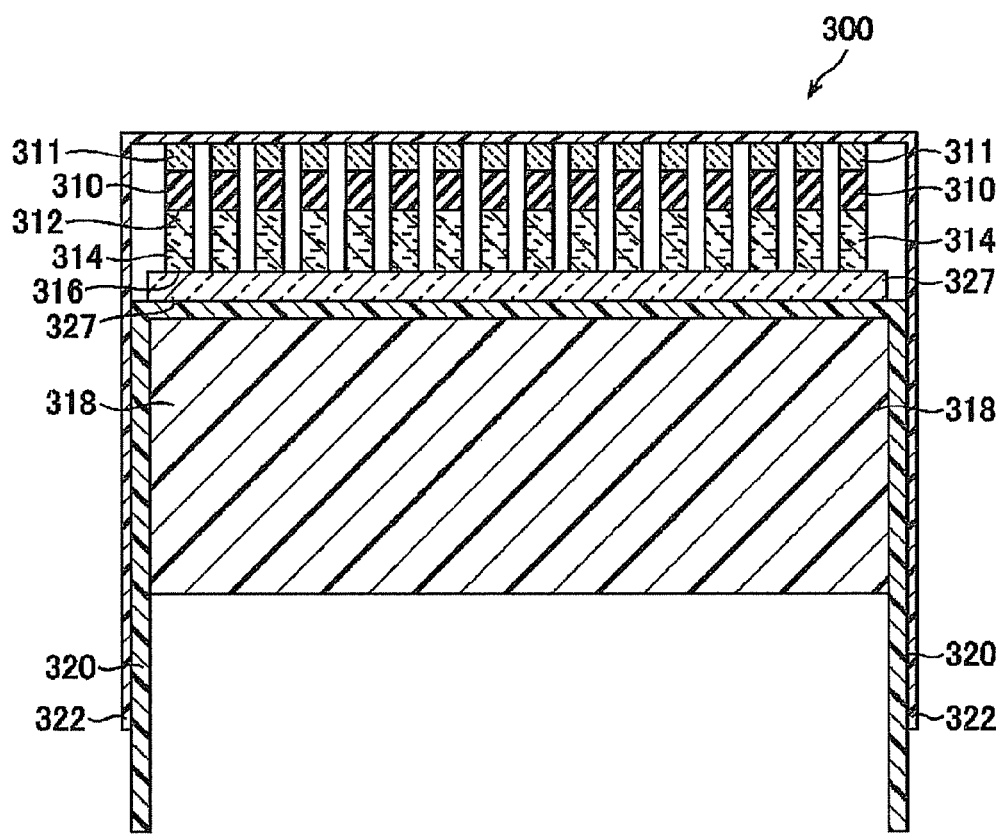
FIG. 6 is an overview cross-section diagram showing a conventional ultrasound transducer which is provided in an ultrasound probe, an electronic circuit and a wiring board connecting them.
Figure 7:
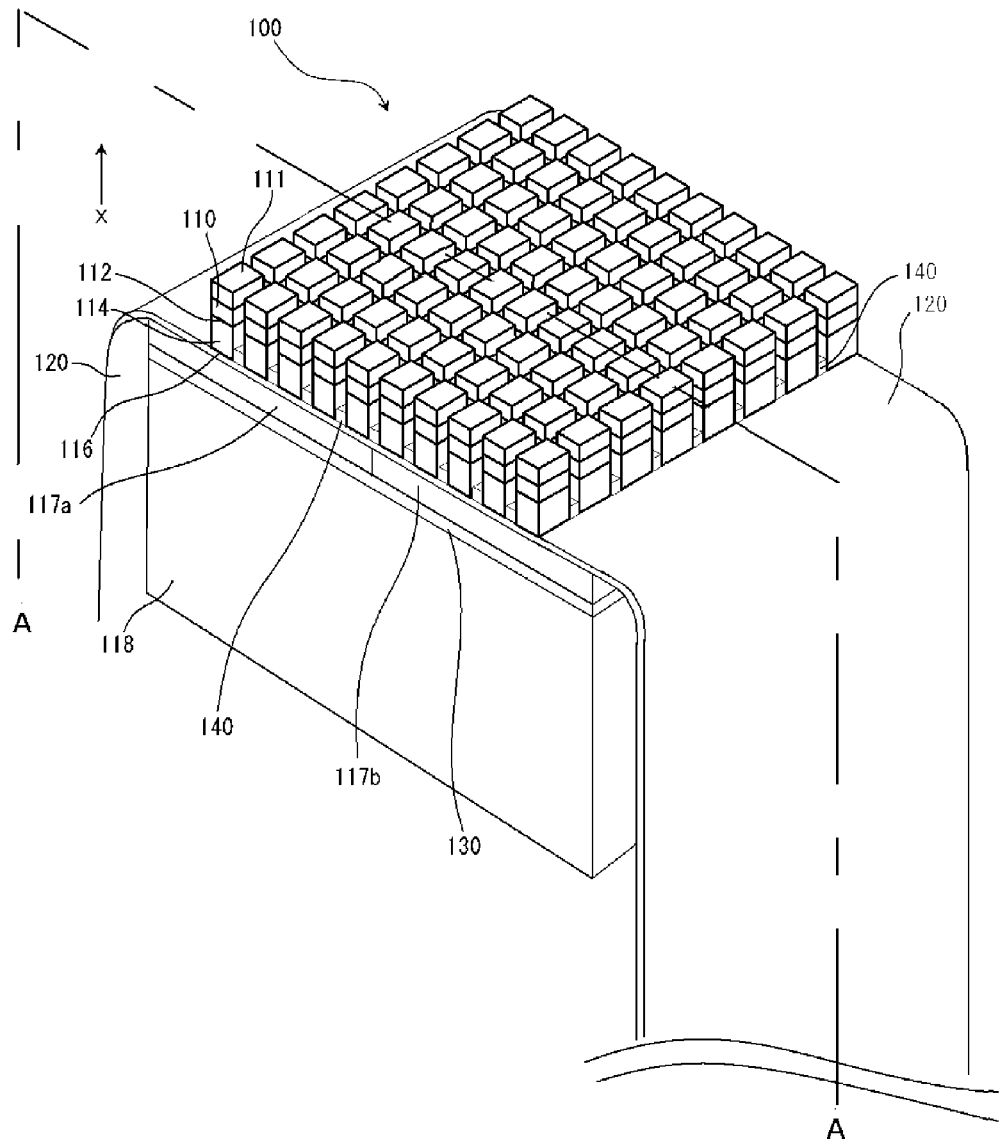
FIG. 7 is an overview perspective diagram showing the state in which the ultrasound transducer according to an embodiment is viewed from the side.
Figure 8:
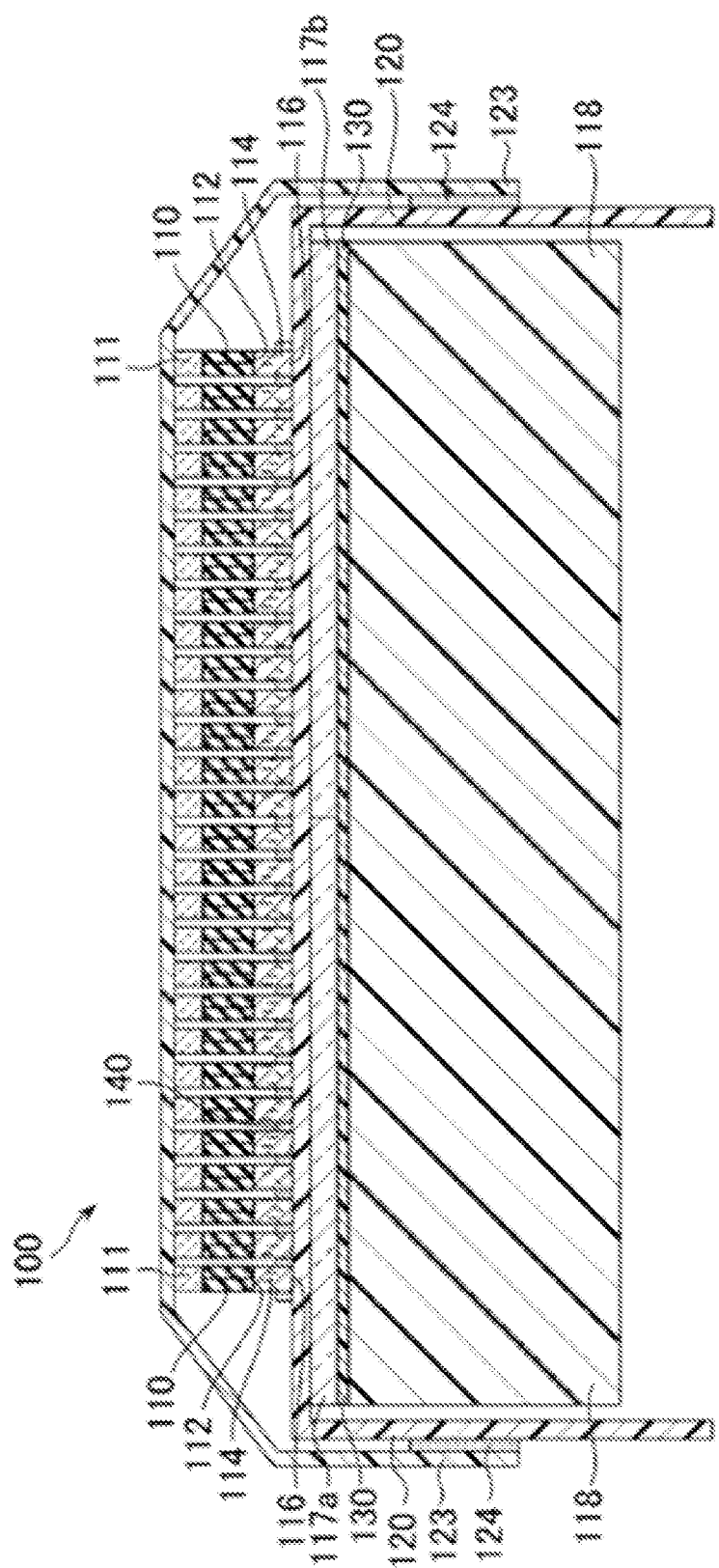
FIG. 8 is an overview A-A cross-section diagram of the ultrasound transducer 100 in FIG. 7.

FIG. 7 is an overview perspective diagram showing the state in which the ultrasound transducer 100 according to the present embodiment is viewed from the side. Moreover FIG. 8 is an overview cross-section diagram of the ultrasound transducer 100 in FIG. 7. Next the configuration of this ultrasound transducer 100 is explained. For the ultrasound transducers 100 shown in each figure, the number of arrays of ultrasound vibrators 114 is different, but this number of arrays is no more than a conceptual number.

(Overview Configuration of Ultrasound Transducer)

As shown in FIG. 7, in the ultrasound transducers 100, the first acoustic matching layer 110 is provided adjacently to the ultrasound vibrators (piezoelectric transducers, etc.). Additionally the second acoustic matching layer 111 is provided adjacently to the surface on the opposite side to that of the ultrasound vibrators 114 of the first acoustic matching layer 110. Moreover, the backing material 118 (load phase) is provided on the opposite side to that of the ultrasound vibrators 114 of the first acoustic matching layer 110. Between the backing material 118 and ultrasound vibrator 114, a flexible printed circuit 120, electronic circuits (117a, 117b) and a rear surface matching layer 130 are provided in the direction from the ultrasound vibrators 114 to the backing material 118a.

As shown in FIG. 7, in the ultrasound vibrators 114, front surface electrodes 112 are provided on the front surface adjacent to the first acoustic matching layer 110. Additionally, rear surface electrodes 116 are provided on the rear surface opposite to this front surface. In the present embodiment, for example, the front surface electrodes 112 may be treated as ground electrodes. Moreover, each front surface electrode 112 is connected in a shared manner using the wiring patterns (not shown in the diagram) formed on the wiring board 123.

The wiring patterns on the wiring board 123 are connected to the wiring patterns of the flexible printed circuit 120 through the conductive adhesion part 124, as shown in FIG. 8. The conductive adhesion part 124 conducts electricity between the wiring board 123 and the flexible printed circuit 120. With such a configuration, through these wiring patterns, signals are transmitted between the ultrasound imaging apparatus main unit and the front surface electrodes 112.

With the ultrasound transducer 100, through the flexible printed circuit 120 and the wiring board 123, a voltage is applied to the front surface electrodes 112 and the rear surface electrode 116. This applied voltage is based on signals transmitted from the ultrasound imaging apparatus main unit. For each of the ultrasound vibrators 114, this applied pressure is converted to ultrasound pulses. The converted ultrasound pulses are transmitted to the subject through the first acoustic matching layer 110, the second acoustic matching layer 111 and the acoustic lens (not shown in the diagrams). The ultrasound transducer 100 receives reflected waves from the subject, and converts the reflective waves to signals. These signals, through the rear surface electrodes 116, are transmitted respectively to the corresponding electronic circuit 117a or electronic circuit 117b. The electronic circuits 117a and 117b perform additive processing on these signals, and reduce the number of signal paths. Moreover, the electronic circuits 117a and 117b transmit the processed signals, through the flexible printed circuit 120, to the ultrasound imaging apparatus main unit. A detailed explanation follows.

The ultrasound vibrators 114 can be made from piezoelectric transducers, etc., using PZT (Lead zirconate titanate/Pb (Zr, Ti)O3), barium titanate (BaTiO3), PZNT (Pb(Zn1/3Nb2/3)O3-PbTiO3) single crystals, PMNT (Pb(Mg1/3Nb2/3)O3-PbTiO3) single crystals, etc.

Moreover, the flexible printed circuit 120 is applicable as one example of the "circuit board". Below, the configuration of each part of the ultrasound transducer 100 is explained.

(Configurations of Parts Between Ultrasound Vibrators and Backing Material)

Figure 9:
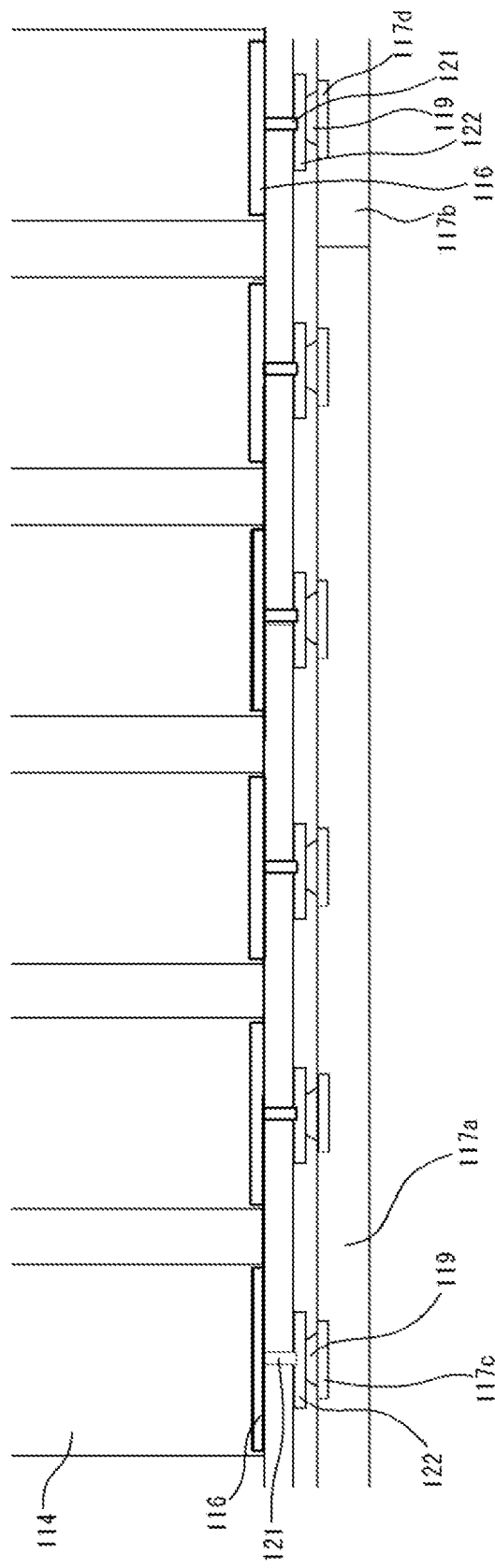
FIG. 9 is an overview, partially enlarged, cross-section diagram of FIG. 8 that shows, in an ultrasound transducer according to an embodiment, a connection state of rear surface electrodes, a flexible printed circuit and electronic circuits.

The configurations of the parts in the ultrasound transducer 100 between the rear surface of the ultrasound vibrators 114 and the front surface of the backing material 118 is now explained using FIG. 7 to FIG. 9. FIG. 9 is an overview, partially enlarged, cross-section diagram of FIG. 8 that shows the connection state of the rear surface electrodes 116, the flexible printed circuits 120 and the electronic circuits 117a and 117b.

As shown in FIG. 7 and FIG. 8, flexible printed circuits 120 are provided adjacent to the rear surface of the ultrasound vibrator 114.

For the flexible printed circuit 120, so-called FPC (Flexible Printed Circuits) may be used. Moreover, wiring patterns not shown in the diagrams are formed on the flexible printed circuits 120. The flexible printed circuits 120, through these wiring patterns, receive from the ultrasound imaging apparatus main unit signals for the purpose of performing transmission of ultrasound pulses. Moreover, the flexible printed circuits 120 transmit to the ultrasound imaging apparatus main unit signals received from the subject. With the present embodiment, wiring patterns are provided on the surface of the flexible printed circuit 120 on the backing material 118 side. However, the location at which the wiring patterns are provided is not limited to the surface of the backing material 118 side; it may be the surface of the ultrasound vibrators 114 side, or it may be both of these surfaces. In addition, the conducting of electricity between the front surface and rear surface of the flexible printed circuit 120 is performed using a through hole or via hole, etc.

Moreover, as shown in FIG. 7 and FIG. 8, the electronic circuits 117a and 117b are provided adjacent to the surface, of the backing material 118 side, of the flexible printed circuit 120. As the electronic circuits 117a and 117b, for example, bare chips having a thickness of approximately 0.05 mm to 0.3 mm are used. If the thickness of the electronic circuits 117a and 117b is reduced to the order of 0.05 mm to 0.3 mm, then even if they are bare chips configured from silicon wafers, as a result of the gap in acoustic characteristics between the ultrasound vibrators 114 and the backing material 118, it is possible to minimize the effect on the transmission and reception of ultrasound as much as possible. In that way, it is possible to avoid a situation in which the ultrasound images are negatively affected.

The minimum value within the abovementioned thickness range for the electronic circuits 117a and 117b, namely "approximately 0.05 mm", is an example of a manufacturing limit. In contrast with this, the upper limit, namely "approximately 0.3 mm", is within the acceptable range for the acoustic characteristic impedance gap between the ultrasound vibrators 114 and the backing material 118.

Moreover, as shown in FIG. 7 and FIG. 8, the electronic circuits 117a and 117b are disposed between the ultrasound vibrators 114 and the backing material 118. In addition, the electronic circuit 117a and the electronic circuit 117b are disposed such that they are aligned in a direction that is orthogonal to the direction from the backing material 118 to the ultrasound vibrators 114. When the electronic circuits 117a and 117b are thus disposed in parallel, as shown in FIG. 7 and FIG. 8, the sum of the length of the electronic circuit 117a and the length of the electronic circuit 117b is longer than the length from one end of the entire 2D array of ultrasound vibrators 114 to the other end. Below, at least one of the electronic circuits 117a and 117b may be described as "electronic circuit 117".

As a first example, the electronic circuit 117 may be configured as a switch circuit. In this case, for example, the entire 2D array consisting of all of the ultrasound vibrators 114 in the ultrasound transducer 100 can be divided into a plurality of M×N blocks (subarrays, etc.), and can be configured to perform ultrasound transceiver control with this electronic circuit 117. In this case, the number of signal paths transmitted to the phasing and addition circuits (not shown in the diagrams) can be greatly reduced.

As one example, the case is considered of an ultrasound transducer 100 being configured with 3072 ultrasound vibrators 114 in a 2D array, and being controlled by dividing this 2D array into 16 blocks by means of an electronic circuit 117. In this case, the number of signal paths from the rear surface electrodes 116 of the ultrasound vibrators 114 is 3072. The electronic circuit 117 batches the 3072 signal paths into 16 blocks, reducing them to 192 paths. Hence, even if the number of ultrasound vibrators 114 in an ultrasound transducer 100 with a 2D array is very large, the pitch of the wiring patterns of the flexible printed circuit 120 will not be overly narrow. As a result, the wiring is simplified between the ultrasound vibrators 114 and the transmitting/receiving circuit (beam former, etc.), which performed the phasing and addition. In addition, it is possible to avoid cross talk between the wiring patterns.

As a second example, it is also possible to configure the electronic circuit 117 as a phasing and addition circuit. In this case, the electronic circuit 117 receives and amplifies the signals converted by each ultrasound vibrator 114, and after performing delayed processing that causes a delay for a prescribed delay amount on each of a plurality of signal lines, performs phasing and addition by implementing additive processing, having batched the relevant plurality of signals into one signal, and additionally converts it into a digital signal, treating it as received data. Furthermore, the processes performed by the electronic circuit 117 are not limited to this, and it can be configured to perform phasing and addition after digitalizing the signals converted by each ultrasound vibrator 114.

Specifically, after the electronic circuit 117 stores in memory a detected signal that has been digitalized, for this detected signal, a delay time for deflection in order to scan the subject is given, by means of an ordered modification of a focusing delay time for the purpose of focusing the ultrasound reflected waves from a prescribed depth, and the reception directionality of ultrasound reflected waves.

In addition, with output that has undergone such beam forming, the electronic circuit 117 implements the phasing and addition processing, namely the processing of phase matching and addition of received signals obtained from a prescribed direction. These detected signals, which have thus undergone phasing and addition, are sent, through connected portion of the electronic circuits 117a and 117b and the flexible printed circuit 120, to the wiring patterns (not shown in the diagrams) of the flexible printed circuit 120. In addition, these detected signals are transmitted to the ultrasound imaging apparatus main unit. In this way, by treating the electronic circuits 117a and 117b as phasing and addition circuits, it is possible to significantly reduce the number of wiring patterns in the flexible printed circuit 20, and implementation is further simplified.

As a third example of the electronic circuit 117, it is possible to configure the electronic circuit 117 as a low noise amplifier (LNA), filter or A/D converter. If the electronic circuit 117 is configured as a low noise amplifier, the electronic circuit 117 amplifies signals from each of the ultrasound vibrators 114 according to the gain that has been set. If the electronic circuit 114 is configured as a filter, it implements a prescribed filter process on the received signals. If the electronic circuit 117 is configured as an A/D converter, it performs digitalization processing on the received signals. The electronic circuit 117 may be assigned only one of the functions, namely low noise amplifier, filter or A/D converter, or it may be an arbitrary combination of these.

As a fourth example of the electronic circuit 117, it is possible to configure the electronic circuit as a transmission circuit. In this configuration, the electronic circuit 117 functions as a pulsar circuit, repeatedly generating a rate pulse for the purpose of forming ultrasound to be transmitted at a prescribed rate frequency fr Hz (cycles; 1/fr second). Moreover, the electronic circuit 117 functions as a transmission delay circuit that focuses the ultrasound into a beam for each channel, and applies to each rate pulse a delay time necessary for deciding on the transmission directionality. Moreover, the trigger generation circuit functions as a trigger generation circuit that applies a drive pulse to the ultrasound vibrators at a timing based on the rate pulse. In addition, it is possible to use the electronic circuit 117 by arbitrarily combining the above example one to example four.

The electronic circuit 117, the flexible printed circuit 120, and the rear surface electrodes 116 of the ultrasound vibrators 114 are connected according to a structure such as the one shown in FIG. 9.

Specifically, connection pads (not shown in the diagrams) are provided on the front surface side of the flexible printed circuit 120 in the same array as the 2D array of ultrasound vibrators 114 of the ultrasound transducer 100. Additionally, penetrating electrodes 121 (through hole or bare hole), as shown in FIG. 9, are provided for these connection pads. As a result of this, the connection pads on the front surface side of the flexible printed circuit 120, by means of the penetrating electrodes 121, are electrically connected with the rear surface side of the flexible printed circuit 120 (on the backing material 118 side).

As shown in FIG. 9, connection pads 122 are provided on the rear surface side of the flexible printed circuit 120, corresponding to the placement locations of the penetrating electrodes 121. Hence, along with the fact that the connection pads 122 are arranged corresponding to the penetrating electrodes 121, they are also arranged on the relevant rear surface side in an array corresponding to the ultrasound vibrators 114. Moreover, in the same way, first terminal electrodes 117c are provided on the front surface side of the electronic circuits 117a, in an array corresponding to the connection pads 122 on the rear surface side of the flexible printed circuit 120. Similarly, first terminal electrodes 117d are provided on the electronic circuit 117b in an array corresponding to the connection pads 122. Furthermore, the first terminal electrodes 117c and 117d of the present embodiment refer to a row of "terminal electrodes".

In addition to the first terminal electrodes 117c and 117d being aligned with the connection pads 122 of the flexible printed circuit 120, for example, by mounting a flip chip, they are connected by means of the conductive connection part 119, as shown in FIG. 9 and FIG. 10.

The conductive connection part 119 consists of conductive bumps. Furthermore, although it is not shown in the figures, in order to secure the mechanical connection strength of the flexible printed circuit 120 and the electronic circuit 117, in the periphery of the conductive connection part 119, the flexible printed circuit 120 and the electronic circuit 117 may also be bonded and reinforced with resin.

Hence, the electronic circuits 117a and 117b, through the first terminal electrodes 117c and 117d, the conductive connection part 119, the connection pads 122, the penetrating electrodes 121, and the connection pads (not shown in the diagrams) on the front surface side of the flexible printed circuit 120, are electrically connected with each rear surface electrode 116 of the ultrasound vibrators 114.

Additionally, second terminal electrodes 117e and 117f are provided on a part that does not overlap with the rear surface electrodes 116 on the front surface side of the electronic circuits 117a and 117b. This "part that does not overlap" means the part that is even further out than the outermost row or column of ultrasound vibrators 114 in the 2D array of ultrasound vibrators 114. For example, describing this in terms of FIG. 8, the "part that does not overlap" refers to the part that is even further to the right than the ultrasound vibrators 114 on the right edge, and the part that is even further to the left than the ultrasound vibrators 114 on the left edge. In other words, the "part that does not overlap" is a part that is made to overlap with a part on which ultrasound vibrators 114 are not present. Furthermore, if elements that are not driven (acoustically ineffective elements) are arrayed outside of the 2D array of ultrasound vibrators 114, the part where these elements overlap with the front surface side of the electronic circuits 117a and 117b is also included in the "part that does not overlap".

The second terminal electrodes 117e and 117f output the detection signals processed by the electronic circuits 117a and 117b to the wiring patterns of the flexible printed circuit 120. Specifically, in the same way as the connection of the first terminal electrodes 117c and 117d, the second terminal electrodes 117e and 117f are electrically connected, by means of the conductive connection part 119, to the connection pads 122 of the flexible printed circuit 120. Furthermore, the second terminal electrode 117f is omitted from the figures. The connection pads 122, which are connected to the second terminal electrode 117e and 117f, are connected to wiring patterns of the flexible printed circuit 120. The signals output from the electronic circuit 117a and 117b, through the relevant wiring patterns, are transmitted to the ultrasound imaging apparatus main unit.

Furthermore, the connection pads 122 connected to the second terminal electrodes 117e and 117f are one example of a "terminal".

The electronic circuits 117a and 117b of the present embodiment are in a configuration that exposes the first terminal electrodes 117c and 117d, and the second electrodes 117e and 117f only to the front surface of the ultrasound vibrators 114 side. Hence, there is no need to form penetrating electrodes (through holes, bare holes, etc.) on the electronic circuits 117a and 117b, and there is no need to expose the electrodes to the rear surface side. Consequently, if a bare chip of a silicon wafer is used as the electronic circuit 117, by means of, for example, grinding the silicon layer of the rear surface side, it is possible to form, for example, an extremely thin chip, on the order of 50 μm. As a result, it is possible to reduce as much as possible the effects on the sending and receiving of ultrasound, and to avoid a situation that proves disadvantageous for ultrasound imaging.

From the above, the ultrasound transducer 100 has the following effects when reflected waves are received from the subject. First, the reflected waves that are received are converted to electrical signals by each ultrasound vibrator 114. These electrical signals pass through the penetrating electrodes 121 from the rear surface electrodes 116 through the connection pads (not shown in the diagrams) on the front surface side of the flexible printed circuit 120. Additionally, these signals are transmitted to the connection pads 122 of the flexible printed circuit 120 from the penetrating electrode 121. The electrical signals transmitted to the connection pads 122 are transmitted to the electronic circuits 117a and 117b through the conductive connection part 119 and the first terminal electrodes 117c and 117d. The electronic circuits 117a and 117b perform any of the abovementioned processes. The signals batched by the electronic circuits 117a and 117b are output to the corresponding connection pads 122 through the second terminal electrodes 117e and 117f of the electronic circuits 117a and 117b.

Moreover, a rear surface matching layer 130 is provided on a surface even further to the rear of electronic circuits 117a and 117b, specifically, between the electronic circuits 117a and 117b and the backing material 118, as shown in FIG. 8. The rear surface matching layer 130 is formed so as to be even thinner than electronic circuits 117a and 117b. The rear surface matching layer 130 has a smaller acoustic characteristic impedance than the backing material 118, and a more lightweight material than electronic circuits 117a and 117b is used. Materials having such characteristics include those in which resins such as polyimides, polyesters, etc., are molded into a film.

With such a rear surface matching layer 130, it is possible to reduce the gap in acoustic characteristics between the backing material 118 and the electronic circuit 117. As a result, even if between the ultrasound vibrators 114 and the backing material 118 there is present a structure of the flexible printed circuit 120 and the electronic circuits 117, it is possible to reduce or eliminate the effect of the mismatch in acoustic characteristics on the sending and receiving of ultrasound.

Moreover, the flexible printed circuit 120 and the ultrasound imaging apparatus main unit are connected, for example, by a configuration such as the following. Specifically, a cable connection board is provided on one edge side of the flexible printed circuit 120, and to this cable connection circuit board is connected the other end of the cable that is connected to the ultrasound imaging apparatus main unit. Additionally, the connectors of the cable connection board are connected to the wiring patterns of the flexible printed circuit 120.

With such a configuration, the signals batched by the electronic circuits 117a and 117b are transmitted to the ultrasound imaging apparatus main unit through the wiring patterns of the flexible printed circuit 120, the cable connection board and the cable.

Moreover with the ultrasound transducer 100 of the present embodiment, connection pads (not shown in the diagrams) on the front surface side of the flexible printed circuit 120 are connected directly to the rear surface electrodes 116 of the ultrasound vibrators 114, but they are not limited to this. For example, it is also possible to deploy a configuration that provides a conductive intermediate matching layer (not shown in the diagrams) on the rear surface side of the ultrasound vibrators 114, and electrically connects the rear surface electrodes 116 with the connection pads on the front surface side of the flexible printed circuit 120. This intermediate matching layer may utilize a material with higher impedance than the ultrasound vibrators 114 formed from a single PZNT crystal or a single PMNT crystal. For example, metallic carbides such as tungsten carbide, or heavy metals including platinum, iridium, etc., may be used. Moreover, the length of the intermediate matching layer in the direction from the backing material 118 to the ultrasound vibrators 114, specifically the thickness of the intermediate matching layer, varies depending on the material, but is on the order of about ¼ wavelength. By providing an intermediate matching layer, a situation in which the ultrasound transducer 100 irradiates ultrasound on to the rear surface side is avoided, and it becomes possible to improve the directionality of the ultrasound beam.

(Backing Material)

As shown in FIG. 7 and FIG. 8, the length of the backing material 118 in a direction orthogonal to the direction from the backing material 118 to the ultrasound vibrators 114 is formed so as to be longer than the length from one edge of the entire 2D array of ultrasound vibrators 114 to the other edge. By forming the backing material 118 so that it is wider than the ultrasound vibrators 114 in this way, the parallel disposed electronic circuits 117a and 117b are supported from the rear surface side.

Moreover, the backing material 118, when transmitting an ultrasound pulse, by absorbing the ultrasound pulse irradiated in a direction opposite to the ultrasound irradiation direction, suppresses excess vibration for each of the ultrasound vibrators 114. From such a perspective, if a bare chip from a silicon wafer is used as electronic circuits 117a and 117b, it is possible to use, as a backing material, porous ceramic infused with a resin such as epoxy. A backing material 118 that is made from such a material (about 10 to 15 MRayl) is matched with a silicon wafer (about 19 MRayl) and adequate damping can be obtained.

(Acoustic Matching Layers)

As shown in FIG. 7 and FIG. 8, with the ultrasound transducer 100, from the front surface of the ultrasound vibrators 114 in the direction of the ultrasound irradiation (the X direction in FIG. 7 and FIG. 8), in order, the first acoustic matching layer 110 and the second acoustic matching layer 111 are layered. The first acoustic matching layer 110 and the second acoustic matching layer 111 match the acoustic characteristic impedance between each ultrasound vibrator 114 and the subject.

The case is now explained of a configuration in which the front surface electrodes 112 are treated as ground electrodes, and by means of the wiring patterns (not shown in the diagrams) formed on the wiring board 123 shown in FIG. 8, the front surface electrodes 112 are connected in a shared manner. In this case, as shown in FIG. 8, it is necessary to dispose the wiring board 123 at a position even further to the front surface side than the second acoustic matching layer 111, and electrically connect the wiring patterns of the wiring board 123 with the front surface electrodes 112. For this purpose, the first acoustic matching layer 110 and the second acoustic matching layer 111 are formed from a conductive material, or they are configured to have leads that connect the wiring patterns and the front surface electrodes 112, etc. As this conductive material, for example, it is possible to use a material containing carbon.

When the wiring board 123 is disposed at a position further to the front surface side than the second acoustic matching layer 111 in this way, no unnecessary structures intervene between the ultrasound vibrators 114 and the acoustic matching layers (110, 111), so it is possible to reduce the acoustic effects due to the presence of the wiring board 123. Moreover, in the present embodiment, the acoustic matching layers (110, 111) are provided in two layers, but the number of layers is not limited to this, and it is possible, for example, to provide only a single acoustic matching layer. Furthermore, if the wiring board 123 is configured from an FPC such that polyimides, etc., are the main material, the use of two acoustic matching layers as in the present embodiment is believed to be preferable from an acoustic matching perspective.

The transmission of signals to the front surface electrodes 112 is performed through the acoustic matching layers (110, 111) and the wiring patterns of the wiring board 123. Specifically, as shown in FIG. 8, the wiring patterns are electrically connected with the flexible printed circuit 120 by means of the conductive adhesion part 124 that is provided on the wiring board 123. Additionally, the wiring patterns of the flexible printed circuit 120 are electrically connected with the ultrasound imaging apparatus main unit.

(Manufacturing Process)

Figure 10B:
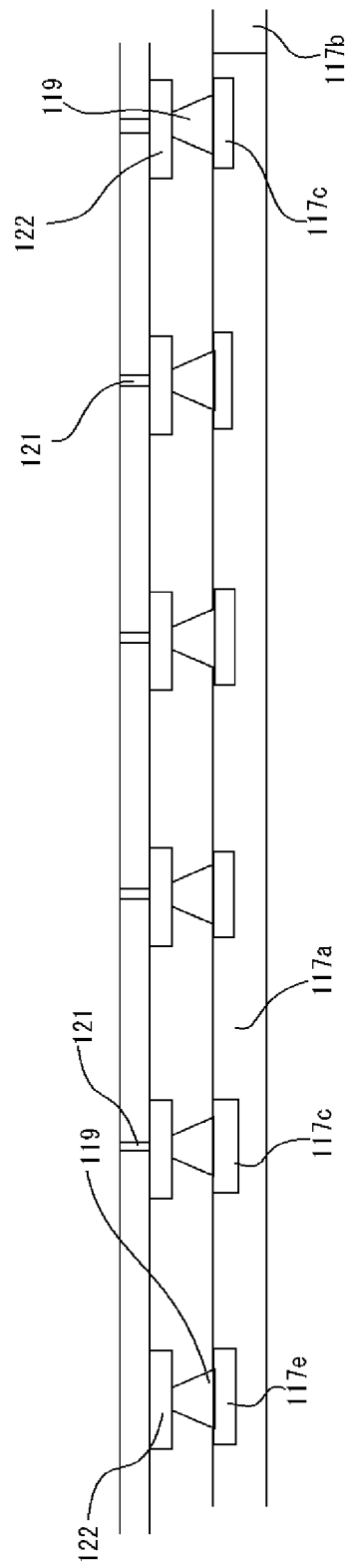
FIG. 10B is an overview cross-section diagram showing, in an ultrasound transducer according to an embodiment, a state in which, after the process shown in FIG. 10A, connection pads and conductive connection parts are connected.

Referring to FIG. 7, FIG. 9 and FIG. 10, the process of manufacturing the ultrasound transducer of the present embodiment is now explained. FIG. 10A is an overview cross-section diagram showing a state in which, in the process of manufacturing the ultrasound transducer 100, the connection pads 122 of the flexible printed circuit 120 and the conductive connection part 119 of the electronic circuit 117 are aligned. FIG. 10B is an overview cross-section diagram showing a state in which, after the process shown in FIG. 10A, the connection pads 122 and the conductive connection part 119 are connected.

(Step 1)

As shown in FIG. 10A, penetrating electrodes 121, etc., are formed at prescribed locations in the same array as the ultrasound vibrators 114. The connection pads 122 of the flexible printed circuit 120 and the first terminal electrodes 117c and 117d of the electronic circuits 117a and 117b are aligned, and the connection pads 122 and the second terminal electrodes 117c and 117d are aligned. A conductive connection part 119, for example, in the form of bumps, is formed on the first terminal electrodes 117c and 117d, and the second terminal electrodes 117e and 117f.

(Step 2)

When the alignment of the electronic circuits 117a and 117b with the flexible printed circuit 120 is performed, by flip chip mounting, etc., through the conductive connection part 119, the connection pads, and the first terminal electrodes 117c and 117d and the second terminal electrodes 117e and 117f are connected (FIG. 10B).

(Step 3)

Each ultrasound vibrator 114 is formed by, for example, cutting a 2D array out of a block of piezoelectric material block. In the stage prior to the cutting out, undivided front surface electrodes 112 are formed on the front surface of the block of piezoelectric material. In the same way, on the rear surface of the block of piezoelectric material, undivided rear surface electrodes 116 are formed. In addition, for the ultrasound vibrators 114, along the direction in which the ultrasound is irradiated, in order, the undivided first acoustic matching layer 110 and second acoustic matching layer 111 are layered.

(Step 4)

For the ultrasound vibrators 114 (piezoelectric material block), when the first acoustic matching layer 110 and second acoustic matching layer 111 are formed, a structure (block) can be obtained in which the undivided ultrasound vibrators 114, the first acoustic matching layer 110 and the second acoustic matching layer 111 are layered. On at least the rear surface side of this structure, slits (dividing slits) are formed for the purpose of dividing the structure according to the 2D array of the ultrasound vibrators 114. These dividing slits are formed in a row direction and a column direction.

Moreover, the depth of the dividing slits is set to an extent such that the structure is not completely divided, and specifically, to an extent such that they reach a halfway of the structure.

(Step 5)

When the dividing slits are formed in the rear surface side of the structure, next, the electronic circuits 117 that are connected to the flexible printed circuit 120 are connected to the backing material 118.

(Step 6)

Next, on the rear surface side of the structure in which the dividing slits are formed, an adhesive agents 140 is provided for the purpose of bonding the ultrasound vibrators 114 and the flexible printed circuit 120. The backing material 118 to which the electronic circuits 117 and the flexible printed circuit 120 are connected is bonded to the structure.

(Step 7)

When the structure and the backing material 118 are connected, the structure is divided along the direction in which, from the second acoustic matching layer 111, the acoustic matching layers (110, 111) and the ultrasound vibrators 114 are layered (specifically, the direction opposite to the X direction shown in FIG. 7). This division is performed along the dividing slits that were formed in advance.

(Step 8)

Next, as shown in FIG. 8, the wiring board 123 is disposed even further to the front surface side than the second acoustic matching layer 111, and by means of the wiring patterns (not shown in the diagram) formed on the rear surface side of the wiring board 123, the front surface electrodes 112 are connected in a shared manner.

By providing dividing slits in advance, in this way, when dividing a structure consisting of ultrasound vibrators 114, etc., it is possible to avoid a situation in which the flexible printed circuit 120 and the electronic circuits 117a and 117b are damaged by mistake.

Additionally, there is the benefit that the bonding strength increases when the adhesive agent 140 is inserted into the dividing slits.

Moreover, the manufacturing process explained above is as follows: electronic circuits 117a and 117b are connected with the flexible printed circuit 120; the structure is formed, and dividing slits are formed; the backing material 118 is connected to the electronic circuits 117a and 117b; the adhesive agent 140 is inserted into the dividing slits; and the backing material 118 is connected with the ultrasound vibrator 114. However, the process of manufacturing the ultrasound transducer of the present embodiment is not limited to this.

For example, after forming the structure and forming the dividing slits, the electronic circuits 117a and 117b may be connected to the flexible printed circuit 120. Moreover, after forming dividing slits in the structure and providing the adhesive agent 140, it is possible to perform a process to connect the backing material 118 to the electronic circuits 117a and 117b.

(Actions and Effects)

The actions and effects of the ultrasound transducer 100 of the embodiment described above are now explained.

As described above, with the ultrasound transducer 100 in one example of the embodiment, after reducing the number of signal paths by means of an additive process on a signal by electronic circuits 117a an 117b, the signal is output to the flexible printed circuit 120. Hence, even if there are a very large number of ultrasound vibrators 114, the pitch of the wiring patterns of the flexible printed circuit 120 will not become too narrow. Therefore, wiring of the ultrasound transducer 100 and circuits (beam former, etc.) are simplified. In addition, it is possible to avoid crosstalk between the wiring patterns.

In the embodiment, the electronic circuits 117a and 117b are configured so as to expose the terminal electrodes (117c, 117d, 117e and 117f) to only the front surface of the ultrasound vibrators 114 side.

Hence, there is no need to form penetrating electrodes such as bare holes, etc., in the electronic circuits 117a and 117b. Additionally, there is no need to expose the electrodes to the rear surface side of electronic circuits 117a and 117b. As a result of this, for example, by using a bare chip as electronic circuits 117a and 117b, and grinding the rear surface side, it is possible to form an extremely thin chip. As a result, it is possible to reduce as much as possible the effects of the gap in acoustic characteristics on the sending and receiving of ultrasound, and to avoid a state that is disadvantageous for ultrasound imaging.

If a silicon wafer is used as the electronic circuits 117, by using for the backing material 118 a material in which porous ceramic infused with a resin such as epoxy, it is possible to match the acoustic characteristic impedance between backing material 118 and the silicon wafer. As a result of this, it is possible to obtain adequate damping.

The rear surface matching layer 130 is disposed between the electronic circuits 117a and 117b and the backing material 118. The rear surface matching layer 130 is formed on a film made from, for example, polyimides, polyesters, etc. As a result of this, it is possible to reduce the gap in acoustic characteristics between the backing material 118 and the electronic circuits 117a and 117b. As a result, even if the flexible printed circuit 120 and the electronic circuits 117a and 117b are present between the ultrasound vibrators 114 and the backing material 118, it is possible to reduce or eliminate the effects on the sending and receiving of ultrasound due to the mismatch in acoustic characteristics.

Moreover, with the ultrasound transducer 100 of the present embodiment described above, there is no need for a configuration in which, as a pull-out structure for the leads of the rear surface electrodes 116, between the ultrasound vibrators 114, or between the block of ultrasound vibrators 114, a multiple number of circuit boards for the purpose of the wiring pull-out is sandwiched, and it is possible to avoid the problem in which side lobes arise.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An ultrasound transducer comprising:
    a plurality of ultrasound vibrators having front surface electrodes provided on the front surface in the ultrasound irradiation direction, having rear surface electrodes provided on the rear surface, being the opposite surface to said front surface, and having piezoelectric characteristics;
    a circuit board disposed on said rear surface side of said ultrasound vibrators, and connected directly or indirectly to said rear surface electrodes;
    an electronic circuit connected to the surface of said circuit board on the opposite side to the surface of said rear surface electrodes side, signal paths being made to pass to each of said ultrasound vibrators through said circuit board; and a backing material disposed on said rear surface side of said ultrasound vibrators, and provided so as to sandwich between it and said ultrasound vibrators said circuit board and said electronic circuit.

2. The ultrasound transducer of claim 1, wherein:

on said circuit board, at a position corresponding to the respective electrodes, penetrating electrodes are provided that penetrate from the surface of said irradiation direction to the opposite surface;

terminal electrodes of said electronic circuit are connected to said circuit board at positions corresponding to said penetrating electrodes on the surface of said circuit board side; and from the electrical connection between said penetrating electrodes and said terminal electrodes, said rear surface electrodes and said electronic circuit are electrically connected.

3. The ultrasound transducer of claim 2, wherein:

said electronic circuit is a bare chip;

said circuit board is a flexible printed circuit having flexibility, and a terminal is provided that is connected to said electronic circuit at a part that does not overlap with said rear surface electrodes and that does overlap with said electronic circuit.

4. The ultrasound transducer of claim 1, wherein:

the length of said electronic circuit in the direction from said backing material to said ultrasound vibrators is substantially in a range from 0.05 mm to 0.3 mm.

5. The ultrasound transducer of claim 1, wherein:

said backing material is made of a material with an acoustic characteristic impedance in the range of 10 MRayl to 15 MRayl.

6. The ultrasound transducer of claim 5, wherein:

the material of said backing material is one in which porous ceramic is infused with epoxy, urethane or silicon resin.

7. The ultrasound transducer of claim 1, further comprising:

a rear surface matching layer provided between said electronic circuit and said backing material, having a smaller acoustic characteristic impedance than said backing material, and being shorter than said electronic circuit in the direction from said backing material to said ultrasound vibrators.

8. The ultrasound transducer of claim 7, wherein:

said rear surface matching layer is made of a polyimide or polyester film.

9. The ultrasound transducer of claim 1, further comprising:

a matching layer provided between said ultrasound vibrators and said circuit board, having a higher acoustic characteristic impedance than said ultrasound vibrators, and having electrical conductivity.

10. An ultrasound probe having an ultrasound transducer, said ultrasound transducer comprising:

a plurality of ultrasound vibrators having front surface electrodes provided on the front surface in the ultrasound irradiation direction, having rear surface electrodes provided on the rear surface, being the opposite surface to said front surface, and having piezoelectric characteristics;

a circuit board disposed on said rear surface side of said ultrasound vibrators, and connected directly or indirectly to said rear surface electrodes;

an electronic circuit connected to the surface of said circuit board on the opposite side to the surface of said rear surface electrodes side, signal paths being made to pass to each of said ultrasound vibrators through said circuit board; and a backing material disposed on said rear surface side of said ultrasound vibrators, and provided so as to sandwich between it and said ultrasound vibrators said circuit board and said electronic circuit.

* * * * *